United States Patent
Rode et al.

(10) Patent No.: US 11,136,302 B2
(45) Date of Patent: Oct. 5, 2021

(54) SINGLE STEP PROCESS FOR THE SYNTHESIS OF FURAN DERIVATIVES FROM CARBOHYDRATES

(71) Applicant: COUNCIL OF SCIENTIFIC AND INDUSTRIAL RESEARCH, New Delhi (IN)

(72) Inventors: Chandrashekhar Vasant Rode, Pune (IN); Suhas Hanmant Shinde, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 52 days.

(21) Appl. No.: 16/616,675

(22) PCT Filed: May 9, 2018

(86) PCT No.: PCT/IN2018/050287
§ 371 (c)(1),
(2) Date: Nov. 25, 2019

(87) PCT Pub. No.: WO2018/216030
PCT Pub. Date: Nov. 29, 2018

(65) Prior Publication Data
US 2021/0147374 A1     May 20, 2021

(30) Foreign Application Priority Data
May 26, 2017 (IN) .............................. 201711018555

(51) Int. Cl.
C07D 307/46 (2006.01)
(52) U.S. Cl.
CPC .................................. C07D 307/46 (2013.01)
(58) Field of Classification Search
None
See application file for complete search history.

(56) References Cited

U.S. PATENT DOCUMENTS 6,706,900 B2    3/2004    Grushin et al.

OTHER PUBLICATIONS

Caes, et at., Biomass to Furanics: Renewalbe Routes to Chemicals and Fuels, ACS Sustainable Chem. Eng., 2015, vol. 3, No. 11, pp. 2591-2605, XP055511572.
Wang, et al.. Direct conversion of carbohydrates to 5-hydroxymethylfurfural using Sn-Mont catalyst, Green Chem., 2012, vol. 14, No. 9, pp. 2506-2512, XP002693732.
Verma, et al.. Sustainable pathway to furanics from biomass via heterogeneous organo-catalysts, Green Chem., 2016, vol. 19, No. 1, pp. 164-168, XP055511379.
Hu, et al., Acid-treatment of C5 and C6 sugar monomers/oligomers: Insight into their interactions, Fuel Processing Technology, 2014, vol. 126, pp. 315-323, XP055511629.
Liu, et al.. One-pot, One-step Synthesis of 2,5-Diformylfuran from Carbohydrates over Mo-Containing Keggin Heteropolyacids, ChemSusChem, 2014, vol. 7, No. 12, pp. 3541-3547, XP55451057.
Ghezali et al., A choline chloride/DMSO solvent for the direct synthesis of diformylfuran from carbohydrates in the presence of heteropolyacids, Green Chemistry, 2015, vol. 17, pp. 4459-4464.
Hu et al., Mediating acid-catalyzed conversion of levoglucosan into platform chemicals with various solvents, Green Chemistry, 2012, vol. 14, pp. 3087-3098.
Kashparova et al., The "one-pot" synthesis of 2,5-diformylfuran, a promising synthon for organic materials in the conversion of biomass, Russian Chemical Bulletin, International Edition, 2015, vol. 64, No. 5, pp. 1069-1073.
Lv et al., Direct synthesis of 2,5-diformylfuran from fructose with graphene oxide as a bifunctional and metal-free catalyst, Green Chemistry, 2016, vol. 18, pp. 2303-2307.
Takagaki et al., One-Pot Synthesis of 2,5-Diformylfuran from Carbohydrate Derivatives by Sulfonated Resin and Hydrotalcite-Supported Ruthenium Catalysts, ACS Caalysis, 2011, vol. 1, pp. 1562-1565.
Xiang, et al., A One-Pot Two-Step Approach for the Catalytic Conversion of Glucose into 2,5-Diformylfuran, Catal Lett, 2011, vol. 141, pp. 735-741.
Xu et al., Polyaniline-Grafted VO(acac)2: An Effective Catalyst for the Synthesis of 2,5-Diformylfuran from 5-Hydroxymethylfurfural and Fructose, ChemCatChem, 2015, vol. 7, pp. 1470-1477.
Yang et al., A one-pot approach for conversion of fructose to 2,5-diformylfuran by combination of Fe3O4-SBA-SO3H and K-OMS-2, Green Chemistry, 2012, vol. 14, pp. 2986-2989.
Zhang et al., Production of 2,5-Diformylfuran from Biomass-derived Glucose via One-Pot two-Step Process, BioResources, 2014, vol. 9, No. 3, pp. 4568-4580.

*Primary Examiner* — Samantha L Shterengarts
(74) *Attorney, Agent, or Firm* — Hudak, Shunk & Farine Co. LPA

(57) ABSTRACT

The present invention discloses a single step process for the synthesis of furan derivative from carbohydrate comprises stirring the reaction mixture of carbohydrate in solvent in presence of catalyst at temperature in the range of 170 to 190° C. for the period in the range of 23 to 25 hrs to afford corresponding furan derivative.

6 Claims, No Drawings

SINGLE STEP PROCESS FOR THE SYNTHESIS OF FURAN DERIVATIVES FROM CARBOHYDRATES

FIELD OF THE INVENTION

The present invention relates to a process for synthesis of furan derivatives. More particularly, the present invention relates to a single step, single pot process for the synthesis of 2,5-di(formyl)furan and 5-((methylthio)methyl)-2-furfural from carbohydrates.

BACKGROUND AND PRIOR ART OF THE INVENTION 5-(Hydroxymethyl)furfural (HMF) is a versatile intermediate that can be obtained in good to moderate yield from biomass sources such as naturally occurring carbohydrates, including fructose, glucose, sucrose and starch. 2,5-Diformylfuran (DFF) is one of the most important derivatives of HMF which has huge applications in the synthesis of polymers, antifungal agents, drugs and ligands. DFF can also be used to produce unsubstituted furan. In spite of its proven usefulness, DFF is not readily available commercially. Selective oxidation of HMF is the only industrially feasible route to DFF. However, there is currently only one industrial process exist which use biomass-derived feedstock for bulk production of HMF. Indeed, lab scale purification of HMF has also proved to be a troublesome operation. HMF could be distilled out by long exposure to temperatures but impurities associated with the synthetic mixture tend to form tarry degradation products. A process that converts a carbohydrate to DFF that avoids the costly HMF isolation step would have an economic advantage. In this direction few researchers have attempted carbohydrate conversion to DFF.

5-((methylthio)methyl)-2-furfural (MTMF) is a new class of sulfur derivative of HMF. This molecule presently not having known applications, but in future it may be a valuable intermediate due to its sulfur functionality. The introduction of sulfur may make MTMF a precursor for the synthesis of some pharmaceutical intermediates. Especially, this molecule could be a starting material for the cheap production of Ranitidine (Zantac).

There are some methods existed in the prior art for glucose conversion to DFF however, all of these strategies have used two or more catalysts for separate purpose (oxidation catalyst+dehydration catalyst) with external source of oxygen. The methods reported on fructose conversion to DFF are limited for fructose molecule but not applicable for complex carbohydrates such as glucose or sucrose. Zhang et al. reported a complex homogeneous catalytic system ($AlCl_3.6H_2O/NaBr$ and vanadium compound) assisted with molecular $O_2$ in DMF solvent for DFF formation from glucose (*Bioresources*, 2014, 9, 4568-4580). Xiang et al. achieved one-pot, two-step synthesis of DFF by catalytic conversion of glucose over homogeneous catalyst system $CrCl_3.6H_2O/NaBr/NaVO_3.2H_2O$, and a DFF yield of 55% based on glucose was obtained (*Catal Lett.*, 2011, 141, 735-741). Yang et al, reported a combination of $Fe_3O_4$-SBA-$SO_3H$ and K-OMS-2 successfully catalyzed direct synthesis of DFF from fructose via acid catalyzed dehydration and successive aerobic oxidation in one-pot reaction (*Green Chem.*, 2012, 14, 2986-2989). Ghezhali et al, reported that mixtures of ChCl and DMSO are attractive media to promote the direct conversion of fructose to DFF with 84% yield in the presence of a bifunctional acid/redox catalyst i.e. HPMoV catalyst (*Green Chem.*, 2015, 17, 4459-4464). Kashparova et al. reported two step procedure for synthesis of DFF from fructose using $H_2SO_4$ (10 mol %) as acid catalyst and [Pip*(O)][$BF_4$] as a oxidation agent in ionic liquids (*Russ. Chem. Bull., Int. Ed.*, 2015, 64, 1069-1073). Xu et al, used Amberlyst-15 for the acid-catalyzed dehydration of fructose into HMF, followed by the in situ oxidation of HMF to DFF catalyzed by polyaniline-VO(acac)$_2$ with 71% yield (*ChemCatChem* 2015, 7, 1470-1477).

Article titled "One-pot synthesis of 2,5-diformylfuran from carbohydrate derivatives by sulfonated resin and hydrotalcite-supported ruthenium catalysts" by A Takagaki et al. published in *ACS Catal.*, 2011, 1 (11), pp 1562-1565 reports glucose conversion to DFF with 25% yield in one-pot process using three different catalysts such as hydrotalcite (HT) for glucose isomerisation to fructose, Amberlyst-15 for fructose dehydration to HMF and Ru/HT for HMF oxidation to DFF in $O_2$ atmosphere. Stepwise addition of catalyst improved DFF yield up to 49% from fructose and 25% from glucose, respectively. In this process three different catalysts were used along with an external $O_2$. In addition to that reaction one has to filter once HMF was formed to separate the acid catalyst. Then oxidation catalyst was added for oxidation step which induce operational complications.

Article titled "Direct synthesis of 2,5-diformylfuran from fructose with graphene oxide as a bifunctional and metal-free catalyst" by G Lv et al. published in *Green Chem.*, 2016, 18, 2302-2307 reports graphene oxide, a metal-free carbon based material as an efficient and recyclable bifunctional catalyst in the direct synthesis of DFF from fructose. A DFF yield of 53.0% was achieved in a one pot and one-step reaction ($O_2$, 24 h) and the DFF yield could be further increased to 72.5% in a one pot and two-step reaction ($N_2$, 2 h and $O_2$ 22 h). This process required external $O_2$ (20 mL/min). In addition to that it is limited to fructose (a relatively soft carbohydrate compared to glucose and sucrose) conversion to DFF.

U.S. Pat. No. 6,706,900 disclosed a one-pot, two-step, catalytic process to prepare 2,5-diformylfuran from a source of fructose or other carbohydrates. The 2,5-Diformylfuran is prepared from a source of fructose in a one-pot, two-step reaction, in a single solvent system process, using a vanadium catalyst. In this process two different catalysts such as Bio-Rad AG-50W resin (acid catalyst) and $V_2O_5$ (oxidation catalyst) were used along with external $O_2$. This process is limited to fructose (a relatively soft carbohydrate compared to glucose and sucrose) conversion to DFF.

Article titled "A choline chloride/DMSO solvent for the direct synthesis of diformylfuran from carbohydrates in the presence of heteropolyacids" by W Ghezali et al. published in *Green Chem.*, 2015, 17, pp 4459-4464 reports a choline chloride/DMSO solvent for the direct synthesis of diformylfuran from carbohydrates in the presence of heteropolyacids. The DFF yield of 84% was obtained from fructose under optimized conditions. This process involves use of mix solvent system such as mixture of choline chloride and dimethyl sulfoxide. External $O_2$ is also required for this process. The process is limited to fructose (relatively soft carbohydrate compared to glucose and sucrose) conversion to DFF.

Article titled "One-pot, one-step synthesis of 2,5-diformylfuran from carbohydrates over Mo-containing Keggin heteropolyacids" by Y Liu et al. published in *ChemSusChem* 2014, 7, pp 3541-3547 reports a one-pot strategy for directly converting fructose into 2,5-diformylfuran (DFF) over Mo-containing Keggin heteropolyacids (HPAs) in open air. They reported yield of 69.3% to DFF is over $Cs_{0.5}H_{2.5}PMo_{12}$ polyoxometalate after deliberate optimization of the reaction conditions.

Article titled "Mediating acid-catalyzed conversion of levoglucosan into platform chemicals with various solvents" by X Hu et al. published in Green Chem., 2012, 14, pp 3087-3098 reports acid-catalyzed conversions of levoglucosan to platform chemicals with various solvents. Dimethyl sulfoxide (DMSO) mainly catalyzed the conversion of levoglucosan into 5-(hydroxymethyl)furfural (HMF), 2,5-furandicarboxaldehyde, and the sulfur ether of HMF. DMSO has a low ability to transfer protons, which helps to avoid further contact of HMF with catalytic sites and stabilizes HMF. In this work author provided effect of solvents on dehydration of levoglucosan with Amberlyst 70. They found MTMF as a major product when levoglucosan dehydrated in DMSO with Amberlyst 70. But, they have not quantified the abundance of MTMF in reaction.

There are only three methods existed for glucose conversion to DFF. However, all of these strategies have used two or more catalyst systems for separate purposes (e.g. oxidation catalyst and dehydration catalyst) with external source of oxygen. The methods reported on fructose conversion to DFF are limited for fructose molecule but not applicable for more complex carbohydrates such as glucose or sucrose.

Therefore, there is need in the art to develop a process which will overcome prior arts drawbacks. Accordingly, the present invention provides a cost effective, single catalyst, single solvent; no oxidation source and simple catalytic process that can be convert a series of carbohydrate to DFF without the isolation of HMF.

OBJECTIVES OF THE INVENTION

The main objective of the present invention is to provide a single step, single pot process for the synthesis of furan derivatives from carbohydrates.

Another objective of the present invention is to provide a single step, single pot process for the synthesis of 2,5-di(formyl)furan (DFF) and 5-((methylthio)methyl)-2-furfural (MTMF) from carbohydrates.

SUMMARY OF THE INVENTION

Accordingly, the present invention provides a single step, single pot process for the synthesis of furan derivative from carbohydrate comprises stirring the reaction mixture of carbohydrate in solvent in presence of catalyst at temperature in the range of 170 to 190° C. for a period in the range of 23 to 25 hrs to afford corresponding furan derivative.

The carbohydrate is selected from fructose, glucose or sucrose.

The furan derivative is selected from 2,5-di(formyl)furan (DFF) or 5-((methylthio)methyl)-2-furfural (MTMF).

The catalyst is selected from sulfuric acid ($H_2SO_4$) or Sn-Mont (Tin hydroxide nanoparticles-embedded montmorillonite).

The solvent is selected from Dimethyl sulfoxide (DMSO), N,N-dimethylformamide (DMF), water, 1-butyl-3-methylimidazolium chloride ([Bmim][Cl]) or combination thereof.

The yield of corresponding furan derivative is in the range of 30 to 60%, preferably 30 to 50%.

DETAILED DESCRIPTION OF THE INVENTION

The invention will now be described in detail in connection with certain preferred and optional embodiments, so that various aspects thereof may be more fully understood and appreciated.

In line with the above objectives, the present invention provides a single step, single pot process for the synthesis of furan derivatives selected from 2,5-di(formyl)furan (DFF) and 5-((methylthio)methyl)-2-furfural (MTMF) from carbohydrates.

In an embodiment, the present invention provide a single step, single pot process for the synthesis of furan derivative from carbohydrate comprises stirring the reaction mixture of carbohydrate in solvent in presence of catalyst at temperature in the range of 170 to 190° C. for the period in the range of 23 to 25 hrs to afford corresponding furan derivative.

The carbohydrate is selected from fructose, glucose or sucrose.

The furan derivative is selected from 2,5-di(formyl)furan (DFF) or 5-((methylthio)methyl)-2-furfural (MTMF).

The catalyst is selected from Sulfuric acid ($H_2SO_4$) or Sn-Mont (Tin hydroxide nanoparticles-embedded montmorillonite).

The solvent is selected from Dimethyl sulfoxide (DMSO), N,N-dimethylformamide (DMF), water, 1-butyl-3-methylimidazolium chloride ([Bmim][Cl]) or combination thereof.

The yield of corresponding furan derivative is in the range of 30 to 60%, preferably 30 to 50%.

The 2,5-di(formyl)furan and 5-((methylthio)methyl)-2-furfural are produced directly from carbohydrates (e.g. fructose, glucose and sucrose) in one-pot process with single solvent (DMSO) system. 2,5-di(formyl)furan is produced in high yield (33-48%) from carbohydrates using catalytic amount of concentrated $H_2SO_4$ (10 mol %). While, 5-((methylthio)methyl)-2-furfural is produced in good to moderate yield (36-45%) from carbohydrates using Sn-Mont catalyst.

The process for the synthesis of furan derivative is depicted in scheme 1 below:

Scheme 1: Synthesis of DFF and MTMF from carbohydrates

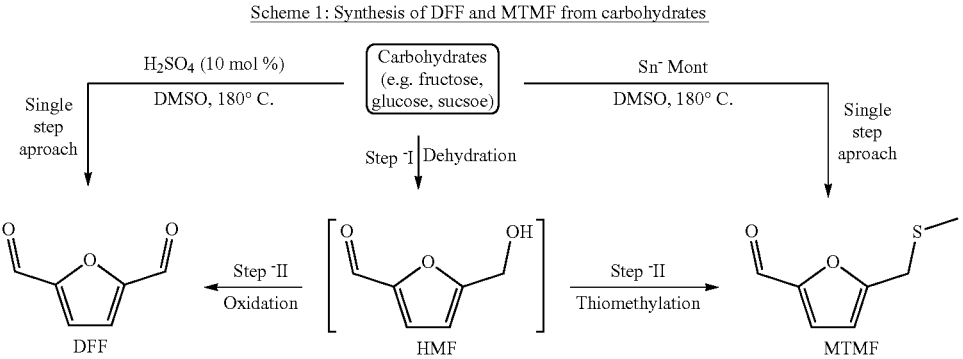

The results are presented in Table 1 shows distribution of dehydration products on different acid catalysts using glucose. Initially, dehydration of glucose is started with the Sn-Mont catalyst at 150° C. in DMSO. After 24 h, glucose is consumed completely with 38% yield of HMF (Table 1, entry 1). Next experiment is performed at 170° C., the product distribution is 19% HMF and 21% MTMF [5-((methylthio)methyl)-2-furfural] (Table 1, entry 2). Interestingly, selectivity to MTMF is increased at 180° C. with 36% yield (Table 1, entry 3). DMSO decomposes at high temperature (180° C.) on Sn-Mont to polysulfides which helped to convert HMF to MTMF. In presence of $SnCl_4.5H_2O$, dehydration followed by chlorination of glucose is facilitating to the 5-(chloromethyl)furfural (Table 1, entry 6). Amberlyst-15 and heteropoly acid ($H_3PW_{12}O_{40}$) are found ineffective for this reaction (Table 1, entry 7, 8). Interestingly, in presence of conc. $H_2SO_4$ glucose is directly converted to DFF in 33% yield. Under experimental conditions DMSO behaves as an oxidation agent as well as reaction medium (Table 1, entry 9).

EXAMPLES

Example 1: Preparation of Sn-Mont

Into an aqueous solution of $SnCl_4.5H_2O$ (0.3 M, 80 mL), montmorillonite (5 g) was added lot wise under stirring at room temperature. After complete addition of montmorillonite, mixture was stirred further for 4 h. Then mixture was filtered, residue was washed with plenty of water (millipore water) until neutral filtrate. Residue was dried in oven at 110° C. for 24 h, ground in mortar pestle and kept in glass bottle.

Example 2: General Procedure for Synthesis of DFF from Carbohydrates

A solution of carbohydrates (fructose/glucose/sucrose, 10 g) in DMSO (10 mL) was heated at 180° C. for 24 h, under stirring in the presence of conc. $H_2SO_4$ (0.54 g or 0.3 mL, 10 mol %). Because small quantities of $Me_2SO_2$ and $Me_2S$ (Unpleasant odour) were produced during the reaction, the outgoing gas was bubbled through bleach (NaOCl) to oxidize the $Me_2S$ and fully destroy the odour. The reaction was monitored by quantitative HPLC analysis with an external standard. Once the highest yield of DFF was achieved, the reaction mixture was cooled to room temperature. Diluted with dichloromethane (300 mL), washed with saturated solution of $NaHCO_3$ (1×100 mL) and water (2×100 mL). Separated organic phase was evaporated and passed through silica (60-120 mesh size). The yield of pure DFF as a yellow

TABLE 1

Catalyst optimization for thermal dehydration of glucose in DMSO [a]

| Entry | Catalyst | Loading | T (° C.) | t (h) | Conv. (%) | Yield (%) [b] HMF | MTMF | DFF |
|---|---|---|---|---|---|---|---|---|
| 1 | Sn-Mont | 0.2 g | 150 | 24 | 100 | 38 | 0 | 0 |
| 2 | Sn-Mont | 0.2 g | 170 | 24 | 100 | 19 | 21 | 0 |
| 3 | Sn-Mont | 0.2 g | 180 | 24 | 100 | 06 | 36 | trace |
| 4 | Sn-Mont | 0.2 g | 180 | 12 | 100 | 30 | 06 | trace |
| 5 | Mont | 0.2 g | 180 | 24 | 61 | 09 | 07 | 0 |
| 6 | $SnCl_4 \cdot 5H_2O$ | 10 mol % | 180 | 24 | 100 | 09 (12)[c] | 0 | 0 |
| 7 | Amberlyst-15 | 0.2 g | 180 | 24 | 71 | 07 | 0 | 0 |
| 8 | $H_3PW_{12}O_{40}$ | 10 mol % | 180 | 24 | 80 | 09 | 06 | 08 |
| 9 | $H_2SO_4$ | 10 mol % | 180 | 24 | 100 | 0 | 0 | 33 |
| 10 | — | — | 180 | 24 | 00 | 0 | 0 | 0 |

[a] Reaction conditions: Glucose (0.5 g, 0.277 mmol), DMSO (10 mL), catalyst.
[b] yields reported on HPLC,
[c] yield of 5-(chloromethyl)-2-furfural The result in table 2 shows dehydration of fructose and sucrose. In DMSO, fructose and sucrose are heated at 180° C. with Sn-Mont, MTMF is produced in 45% and 40%, respectively (Table 2, entry 1 and 2). Similarly, with concentrated $H_2SO_4$ fructose and sucrose are transformed into DFF with 48% and 39%, respectively (Table 2, entry 3 and 4).

TABLE 2

One-pot synthesis of 2,5-diformylfuran and 5-((methylthio)methyl)-2-furfural from carbohydrates in DMSO [a]

| Entry | Substrates | Catalyst | Loading | Conversion (%) | Yield (%) [b] MTMF | DFF | HMF |
|---|---|---|---|---|---|---|---|
| 1 | Fructose | Sn-Mont | 0.2 g | 100 | 45 | 2 | 06 |
| 2 | Sucrose | | | >99 | 40 | 2 | 04 |
| 3 | Fructose | $H_2SO_4$ | 10 mol % | 100 | 0 | 48 | Trace |
| 4 | Sucrose | | | >99 | 0 | 39 | Trace |

[a] Reaction conditions: Carbohydrate (0.5 g), DMSO (10 mL), catalyst, 180° C., 24 h.
[b] yields reported on HPLC.

Following examples are given by way of illustration therefore should not be construed to limit the scope of the invention.

crystalline solid was 2.88 g (42% calculated on fructose used), 1.84 g (27% calculated on glucose used) and 2.24 g (31% calculated on sucrose used).

$^1$H NMR (200 MHz, CDCl$_3$), δ ppm 7.4 (s, 2H, furan H), 9.8 (s, 2H, CHO); $^{13}$C NMR (50 MHz, CDCl$_3$) δ ppm 119.19 (s, 2CH) 154.19 (s, 2C) 179.18 (s, 2CHO).

Example 3: General Procedure for Synthesis of MTMF from Carbohydrates

A solution of carbohydrates (fructose/glucose/sucrose, 10 g) in DMSO (10 mL) was heated at 180° C. for 24 h, under stirring in the presence of Sn-Mont (4 g). Because small quantities of decomposition products of DMSO (Unpleasant odour) were produced during the reaction, the outgoing gas was bubbled through bleach (NaOCl) to oxidize the Me$_2$S and fully destroy the odour. The reaction was monitored by quantitative HPLC analysis with an external standard. Once the highest yield of MTMF was achieved, the reaction mixture was cooled to room temperature and filtered to separate the catalyst. Catalyst bed was washed with dichloromethane (300 mL) further mother liquor was washed with water (2×100 mL). Separated organic phase was evaporated and passed through silica (60-120 mesh size). The yield of pure MTMF as a brown crystalline solid was 3.29 g (38% calculated on fructose used), 2.42 g (28% calculated on glucose used) and 3.0 g (33% calculated on sucrose used).

$^1$H NMR (200 MHz, CDCl$_3$) δ ppm 2.15 (s, 3H) 3.74 (s, 2H) 6.44-6.45 (d, J=3.54 Hz, 1H) 7.20-7.22 (d, J=3.54 Hz, 1H) 9.58 (s, 1H); $^{13}$C NMR (50 MHz, CDCl$_3$) δ ppm 15.81 (s, CH$_3$) 30.38 (s, CH$_2$) 110.23 (s, CH) 122.56 (s, CH) 152.41 (s, C) 159.31 (s, C) 177.30 (s, CHO).

Example 4: Analysis of DFF and MTMF

TLC analysis was performed using Merck 5554 aluminium-backed silica plates, and the compounds were visualized under UV light (254 nm). Conversion of carbohydrates was calculated by using Agilent HPLC (column: Hi-Plex USP L17, detector: RI and mobile phase: millipore water with 0.6 mL/min flow). Yield of dehydration product of carbohydrates calculated by using Agilent HPLC (column: Poroshell 120 EC-C18, 2.7 μm, detector: UV and mobile phase: 0.1% acetic acid in millipore water:acetonitrile (85:15) with 0.6 mL/min flow). Pure products were characterized and confirmed by $^1$H-NMR and $^{13}$C-NMR using CDCl$_3$ (0.01%, TMS) as solvent on 200 MHz frequency Bruker instrument. The products were also confirmed using QP-Ultra 2010 GC-MS Shimadzu instrument, RTX-5 column, helium as carrier gas, EI mode and ionization source temperature 200° C.

Example 5: Thermal Dehydration of Glucose Over Different Acidic Catalysts

Initially, dehydration of glucose was started with the Sn-Mont catalyst at 150 in DMSO. After 24 h, glucose was consumed completely with 38% yield of HMF (Table 1, entry 1). Next experiment was performed at 170° C., the product distribution was 19% HMF and 21% MTMF [5-((methylthio)methyl)-2-furfural](Table 1, entry 2). Interestingly, selectivity to MTMF was increased at 180 with 36% yield (Table 1, entry 3). Presence of Lewis acid and Brønsted acid sites are unique features of Sn-Mont which facilitates the glucose isomerisation to fructose on its Lewis acid sites and dehydration of in-situ formed fructose to HMF on its Brønsted acid sites. DMSO decomposes at high temperature (180° C.) on Sn-Mont to polysulfides which helped to convert HMF to MTMF. In presence of SnCl$_4$.5H$_2$O, dehydration followed by chlorination of glucose was facilitating to the 5-(chloromethyl)furfural (Table 1, entry 6). Amberlyst-1 and heteropoly acid (H$_3$PW$_{12}$O$_{40}$) were found ineffective for this reaction (Table 1, entry 7, 8). Interestingly, in presence of conc. H$_2$SO$_4$ glucose was directly converted to DFF in 33% yield. Under experimental conditions DMSO behaves as an oxidation agent as well as reaction medium (Table 1, entry 9).

TABLE 1

Catalyst optimization for thermal dehydration of glucose in DMSO [a]

| Entry | Catalyst | Loading | T (° C.) | t (h) | Conv. (%) | Yield (%) [b] | | |
|---|---|---|---|---|---|---|---|---|
| | | | | | | HMF | MTMF | DFF |
| 1 | Sn-Mont | 0.2 g | 150 | 24 | 100 | 38 | 0 | 0 |
| 2 | Sn-Mont | 0.2 g | 170 | 24 | 100 | 19 | 21 | 0 |
| 3 | Sn-Mont | 0.2 g | 180 | 24 | 100 | 06 | 36 | trace |
| 4 | Sn-Mont | 0.2 g | 180 | 12 | 100 | 30 | 06 | trace |
| 5 | Mont | 0.2 g | 180 | 24 | 61 | 09 | 07 | 0 |
| 6 | SnCl$_4$•5H$_2$O | 10 mol % | 180 | 24 | 100 | 09 (12)[c] | 0 | 0 |
| 7 | Amberlyst-15 | 0.2 g | 180 | 24 | 71 | 07 | 0 | 0 |
| 8 | H$_3$PW$_{12}$O$_{40}$ | 10 mol % | 180 | 24 | 80 | 09 | 06 | 08 |
| 9 | H$_2$SO$_4$ | 10 mol % | 180 | 24 | 100 | 0 | 0 | 33 |
| 10 | — | — | 180 | 24 | 00 | 0 | 0 | 0 |

[a] Reaction conditions: Glucose (0.5 g, 0.277 mmol), DMSO (10 mL), catalyst.
[b] yields reported on HPLC,
[c] yield of 5-(chloromethyl)-2-furfural

Example 6: Thermal Dehydration of Fructose and Sucrose

In DMSO, fructose and sucrose were heated at 180° C. with Sn-Mont, MTMF was produced in 45% and 40%, respectively (Table 2, entry 1 and 2). Similarly, with concentrated H$_2$SO$_4$ fructose and sucrose were transformed into DFF with 48% and 39%, respectively (Table 2, entry 3 and 4).

TABLE 2

One-pot synthesis of 2,5-diformylfuran and 5-((methylthio)methyl)-
2-furfural from carbohydrates in DMSO [a]

| Entry | Substrates | Catalyst | Loading | Conversion (%) | Yield (%) [b] MTMF | DFF | HMF |
|---|---|---|---|---|---|---|---|
| 1 | Fructose | Sn-Mont | 0.2 g | 100 | 45 | 2 | 06 |
| 2 | Sucrose | | | >99 | 40 | 2 | 04 |
| 3 | Fructose | $H_2SO_4$ | 10 mol % | 100 | 0 | 48 | Trace |
| 4 | Sucrose | | | >99 | 0 | 39 | Trace |

[a] Reaction conditions: Carbohydrate (0.5 g), DMSO (10 mL), catalyst, 180° C., 24 h.
[b] yields reported on HPLC.

Example 7: Parameter Study for the Glucose Conversion to DFF Over $H_2SO_4$ a) Dehydration of Glucose with $H_2SO_4$ (10 Mol %) in Different Solvents:

The basic criterion for the solvent selection is that glucose should soluble in selected solvents. Therefore some solvent such as N,N-dimethylformamide (DMF), $H_2O$ and 1-Butyl-3-methylimidazolium chloride [Bmim] [Cl] were chosen for glucose dehydration reaction. When glucose was dissolved in DMF and 10 mol % $H_2SO_4$ subsequently heated at 180° C. for 24 h. Levulinic acid (09%) was formed along with excess humin after complete consumption of glucose (Table 3, entry 1). On the other hand, under experimental conditions in presence of water, HMF (09%) and levulinic acid (21%) were formed after full glucose conversion (Table 3, entry 2). In presence of 1-Butyl-3-methylimidazolium chloride ([Bmim][Cl]) DFF was not formed at all (Table 3, entry 3). Thus from above experiments it is concluded that, other than DMSO all other solvents were not suitable for the production of DFF from glucose.

TABLE 3

Dehydration of glucose with $H_2SO_4$ (10 mol %) in different solvents [a]

| Entry | Solvents | Conversion | Yield HMF | DFF | LA |
|---|---|---|---|---|---|
| 1 | DMF | 100 | 00 | 00 | 09 |
| 2 | $H_2O$ | 100 | 09 | 00 | 21 |
| 3 | [Bmim][Cl] (3 mL) | 100 | 19 | 00 | 09 |

[a] Reaction conditions: glucose (0.5 g), $H_2SO_4$, solvent (10 mL), 180° C., 24 h.
LA = Levulinic acid.
DMF = N,N-dimethylformamide,
[Bmim][Cl] = 1-Butyl-3-methylimidazolium chloride b) Dehydration of Glucose with Different Concentrations of $H_2SO_4$ in DMSO In the catalyst optimisation study different concentration (5, 15, 20 mol %) of $H_2SO_4$ (Table 4) is screened. With 5 mol % of $H_2SO_4$, glucose was consumed completely with 07% of HMF and 29% DFF (Table 4, entry 1). While using 15 mol % of $H_2SO_4$, DFF was produced in 31% yield (Table 4, entry 2). On the other hand, in presence of 20 mol % of $H_2SO_4$, DFF yield was dropped to 28% (Table 4, entry 3). Higher catalyst concentration than 10 mol % has induced negative effect on DFF yield due to excess humin formation.

TABLE 4

Dehydration of glucose with different concentrations of $H_2SO_4$ in DMSO

| Entry | Concentration of $H_2SO_4$ | Conversion | Yield HMF | DFF |
|---|---|---|---|---|
| 1 | 5 mol % | 100 | 07 | 29 |
| 2 | 15 mol % | 100 | 00 | 31 |
| 3 | 20 mol % | 100 | 00 | 28 |

[a] Reaction conditions: glucose (0.5 g), $H_2SO_4$, DMSO (10 mL), 180° C., 24 h.

c) Dehydration of Glucose with $H_2SO_4$ (10 Mol %) in DMSO at Different Temperature The range of temperatures from 160-190° C. is studied in Table 5. At 160° C., product distribution was 32% HMF and 06% DFF with complete conversion of glucose (Table 5, entry 1). While increasing temperature to 170° C., DFF yield was increased to 17% (Table 5, entry 2). However, at 190° C. DFF was obtained in 31% yield which was comparable to the result obtained at 180° C.

TABLE 5

Dehydration of glucose with $H_2SO_4$ (10 mol %) in DMSO at different

| Entry | Temperature (° C.) | Conversion (%) | Yield (%) HMF | DFF |
|---|---|---|---|---|
| 1 | 160 | 100 | 32 | 06 |
| 2 | 170 | 100 | 21 | 17 |
| 3 | 190 | 100 | 00 | 31 |

[a] Reaction conditions: glucose (0.5 g), $H_2SO_4$, DMSO (10 mL), 160-190° C., 24 h.

Example 8: Parameter Study for the Glucose Conversion to MTMF Over Sn-Mont a) Dehydration of Glucose with Different Sn-Mont Loading in DMSO Effect of Sn-Mont loading was studied for the MTMF production and results are presented in Table 6. When lower than 0.2 g loading of Sn-Mont was used, conversion of glucose wasn't reached to 100% (Table 6, entry 1 and 2). While, more than 0.2 g loading of Sn-Mont was used, MTMF was formed in 38% yield which is comparable to the results obtained with 0.2 g Sn-Mont loading (Table 6, entry 1 and 2). Thus 0.2 g loading was found optimum loading and same amount was used for further experiment.

TABLE 6

Dehydration of glucose with different Sn-Mont loading in DMSO [a]

| Entry | Sn-Mont loading (g) | Conversion (%) | Yield (%) HMF | Yield (%) MTMF |
|---|---|---|---|---|
| 1 | 0.1 | 69 | 17 | 05 |
| 2 | 0.15 | 90 | 19 | 12 |
| 3 | 0.250 | 100 | 00 | 38 |

[a] Reaction conditions: glucose (0.5 g), Sn-Mont, DMSO (10 mL), 180° C., 24 h.

b) Dehydration of Glucose with Sn-Mont in DMSO at Different Temperature

Dehydration of glucose was studied over Sn-Mont at different temperature (160-190° C.) in DMSO solvent (Table 7). At 160° C., product distribution was 30% of HMF and 08% of MTMF (Table 7, entry 1). While at 170° C., product distribution was 19% of HMF and 19% of MTMF (Table 7, entry 2). However, at 190° C., MTMF was obtained in 36% yield which was comparable to the result obtained at 180° C.

TABLE 7

Dehydration of glucose with Sn-Mont in DMSO at different temperature [a]

| Entry | Temperature (° C.) | Conversion (%) | Yield (%) HMF | Yield (%) MTMF |
|---|---|---|---|---|
| 1 | 160 | 100 | 30 | 08 |
| 2 | 170 | 100 | 19 | 19 |
| 3 | 190 | 100 | 00 | 36 |

[a] Reaction conditions: glucose (0.5 g), Sn-Mont, DMSO (10 mL), 160-190° C., 24 h.

ADVANTAGES OF THE INVENTION

1) Single step, single catalyst, single solvent, one-pot process
2) Simple and cost effective process
3) No external 02 required in DFF production.
4) No external source of S is required in MTMF production.
5) No use of external oxygen pressure
6) Isolation of furfural (HMF) is not required.

We claim:

1. A single step, single pot process for the synthesis of a furan derivative from a carbohydrate comprises stirring the reaction mixture of the carbohydrate in solvent in presence of a catalyst at temperature in the range of 170 to 190° C. for a period in the range of 23 to 25 hrs. to afford the corresponding furan derivative comprising 2,5-di(formyl)furan or 5-((methylthio)methyl)-2-furfural.

2. The process as claimed in claim 1, wherein said carbohydrate is selected from fructose, glucose or sucrose.

3. The process as claimed in claim 1, wherein said catalyst is selected from Sulfuric acid or Sn-Mont.

4. The process as claimed in claim 1, wherein said solvent is selected from dimethyl sulfoxide, N,N-dimethylformamide, water, 1-butyl-3-methylimidazolium chloride or combination thereof.

5. The process as claimed in claim 1, wherein the yield of said furan derivative is in the range of 30 to 60%.

6. The process as claimed in claim 1, wherein the yield of said furan derivative is in the range of 30 to 50%.

* * * * *